United States Patent [19]

Malinow et al.

[11] 4,242,502

[45] Dec. 30, 1980

[54] ENHANCEMENT OF CHOLESTEROL COMBINING PROPERTIES OF SAPONINS

[75] Inventors: Manuel R. Malinow, Portland; Phyllis A. McLaughlin, Cornelius, both of Oreg.; George O. Kohler, El Cerrito; Arvin L. Livingston, Martinez, both of Calif.

[73] Assignee: United States of America, Washington, D.C.

[21] Appl. No.: 31,970

[22] Filed: Apr. 20, 1979

Related U.S. Application Data

[63] Continuation of Ser. No. 865,985, Dec. 30, 1977, abandoned.

[51] Int. Cl.² .......................... C07G 3/00; C07J 17/00
[52] U.S. Cl. .......................................... 536/5; 424/182
[58] Field of Search ..................... 536/5, 4; 424/182

[56] References Cited

U.S. PATENT DOCUMENTS 3,992,315  11/1976  Dibbs et al. ............................. 536/5

FOREIGN PATENT DOCUMENTS 506827  10/1954  Canada ......................................... 536/5
559084   6/1958  Canada ......................................... 536/5
974878  11/1964  United Kingdom ....................... 536/5

Primary Examiner—Johnnie R. Brown
Assistant Examiner—Blondel Hazel
Attorney, Agent, or Firm—Holman & Stern

[57] ABSTRACT

The present invention relates to the use of Saponins to inhibit cholesterol absorption. More particularly, the present invention relates to the enhancement of the cholesterol combining properties of saponins, by acid hydrolysis of the saponins under mild conditions.

15 Claims, 1 Drawing Figure

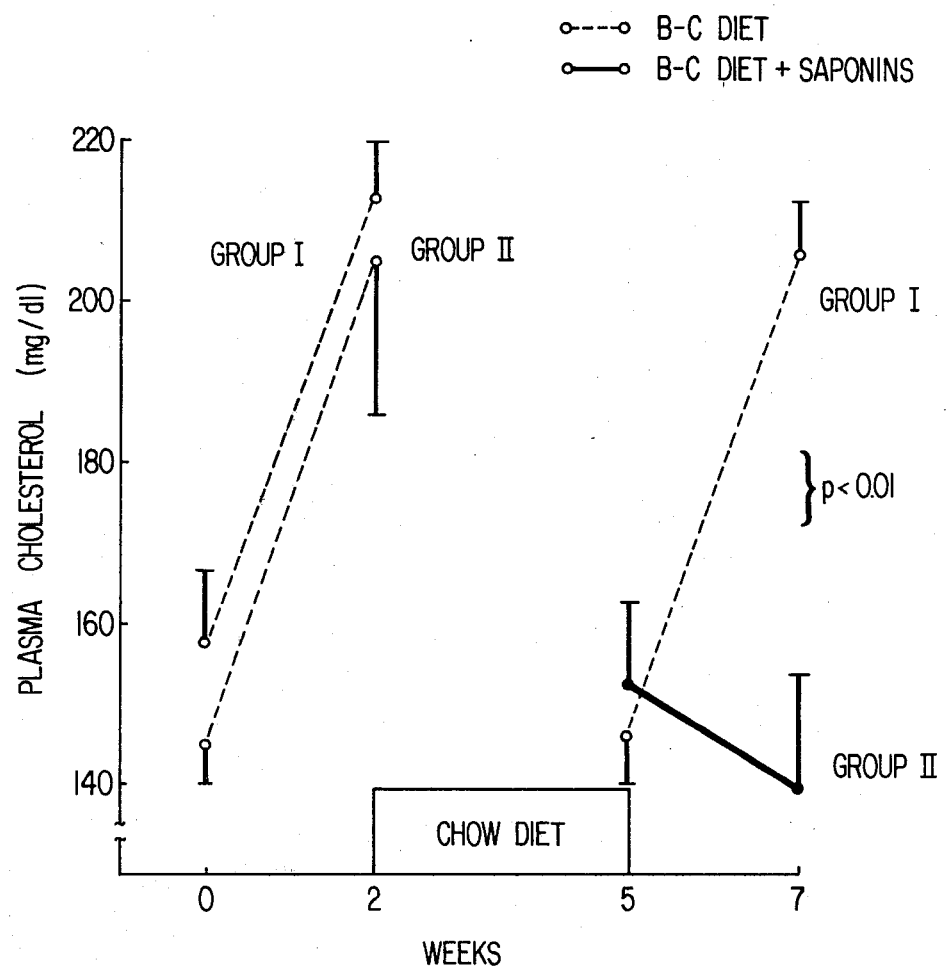

ENHANCEMENT OF CHOLESTEROL COMBINING PROPERTIES OF SAPONINS

The invention described herein was made in the course of work under a grant or award from the Department of Health, Education and Welfare.

This is a continuation of application Ser. No. 865,985, filed Dec. 30, 1977, now abandoned.

BACKGROUND AND SUMMARY OF THE INVENTION

The present invention relates to the use of saponins to inhibit cholesterol absorption. More particularly, the present invention relates to the enhancement of the cholesterol combining properties of saponins, by acid hydrolysis of the saponins under mild conditions.

Saponins from plant sources such as alfalfa have been known to have a variety of biological effects upon various animals. Included among the chemical activities of certain saponins is the ability to form chemical complexes with sterols, including cholesterol. Such activities are described, for example, in the following publications: *Proc. Soc. Exp. Biol. Med.*, 99, 424 (1958); *Poultry Sci.*, 37, 42 (1958); *Poultry Sci.*, 51, 677, (1972); *J. Lipid Res.*, 12, 482 (1971); and *J. Sci. Food Agric.*, 27 (1), 63–72 (1976).

The addition of certain saponins to the diets of some animal has been found to prevent hypercholesterolemia. By the present invention, it has been found that the ability of saponins to prevent hypercholesterolemia may be enhanced at least about five fold by prior treatment of the saponins with acid. Thus the method of the present invention enhances the ability of saponins to inhibit cholesterol absorption and to alleviate hypercholesterolemia. The present method includes mild acid treatment of the saponins. The treated saponins may then be advantageously employed by oral administration to patients with hypercholesterolemia.

BRIEF DESCRIPTION OF THE DRAWINGS

The advantages and features of the present invention will more fully understood from the following description of the preferred embodiments, taken in conjunction with the accompanying drawing, wherein:

the FIGURE of the drawing shows the effect of alfalfa root saponins on plasma cholesterol in monkeys (*Macaca fascicularis*).

DESCRIPTION OF THE PREFERRED EMBODIMENTS

In carrying out the acid hydrolysis of the saponins in accordance with the present invention, the saponins, such as, for example, alfalfa root or top saponins, are isolated from such roots or tops by any suitable method known in the art. One such method is described by R. J. Morris et al., *J. Org. Chem.*, 26, 1241 (1961), which is incorporated herein by reference. Saponins from plants other than alfalfa may also be employed.

The saponins are dissolved in a mixture of water and an alcohol such as ethanol or other suitable alcohol. One such mixture which was employed was a 1:1 mixture by volume of water and ethanol. The solvent mixture may be heated slightly to facilitate dissolving of the saponins. A sufficient amount of acid is added to the solution to provide a solution which is from about 1.2 to about 2.0 N. Any suitable acid such as, for example, hydrochloric acid, nitric acid or sulfuric acid may be employed. The solution is heated with stirring until a slight reflux of solvent is noted. This will be at a temperature of about 90° C. for an ethanol-water (1:1) solution.

The solution is maintained at gentle reflux for approximately 30 minutes. The period of reflux may vary from about 20 minutes to about 60 minutes depending on the acid concentration and extent of reflux. The solution is then cooled and diluted with at least an equal volume of water. The precipitate which forms is collected, preferably by centrifugation, washed with water to remove acid, redissolved in hot alcohol and reprecipitated by the addition of water. It may be desirable to decolorize the alcohol solution of saponin by treatment with charcoal or other suitable discoloring agent. The final product after drying is suitable for addition to sets at practical clinical levels, in amounts of about 2 to 6 g/day.

The following examples illustrate the features of the present invention.

EXAMPLE 1

Nonhydrolyzed and hydrolyzed saponins obtained from alfalfa tops and alfalfa roots were given intragastrically to groups of 6 rats each. The hydrolyzed saponins were prepared as described above in accordance with the present invention. The animals wre injected i.v. with $^3$H-cholesterol and received $^{14}$C-cholesterol intragastrically. Absorbed cholesterol was calculated from measurements of fecal radioactive sterol excretion and $^{14}$C/$^3$H ratio was determined in the nonsaponifiable extract of plasma. Absorbed $^{14}$C-cholesterol was 67±3% (mean±S.E.) of O.D. (oral dose) /72 hr in control rats; 20 mg of hydrolyzed saponins decreased this fraction to 13±2% of O.D./72 hr (p. "t" test <0.001). The relative effect of saponins on cholesterol absorption was: Hydrolyzed saponins (roots)=100; nonhydrolyzed saponins (roots)=16; hydrolyzed saponins (tops)=112; nonhydrolyzed saponins (tops)=25. Results demonstrate that acid hydrolysis of alfalfa saponins enhances their ihibition of cholesterol intestinal absorption.

EXAMPLE 2

In this example, alfalfa root saponins were found to prevent the expected increase in plasma cholesterol associated with the ingestion of a semipurified high-butter, high-cholesterol diet in monkeys. Experiments in rats showed that alfalfa root saponins decrease cholesterol intestinal absorption.

The addition of alfalfa meal-sun-cured alfalfa hay-(*Medicago sativa*) to a cholesterol-containing diet has been known to prevent hypercholesterolemia in rabbits and in monkeys. The substance responsible for this effect has not been identified. Since different saponins from other sources have prevented cholesterol-induced hypercholesterolemia in chickens and cholesterol absorption in rats, a study was made of the effect of alfalfa saponins on the cholesterolemia of cholesterol-fed monkeys.

Observation in Monkeys

Ten adult female cynomolgus monkeys (*Macaca fascicularis*) were selected from a group of 236 animals for their relative hypo-response to a high cholesterol diet. They were fed for two weeks on a semipurified diet containing sucrose (41%), butter (24%), casein (26%), cholesterol (0.1%), and additional minerals and vitamins. Venous blood was obtained before and after the diet, and plasma cholesterol was determined by the method as described by L. L. Rudel et al., *J. Lipid Res.* 14, 364 (1973) incorporated herein by reference. The animals were ranked and stratified according to their increase in cholesterolemia, and randomly assigned to two groups of 5 monkeys each. They were returned to the standard laboratory low cholesterol diet for the following two weeks. During the next two weeks, all monkeys received the semipurified diet; the diet of group II contained 1% of saponins isolated from alfalfa roots and acid hydrolyzed in accordance with the present invention. Plasma cholesterol was determined again, before and after the last dietary period.

Observation in Rats

The same preparation of alfalfa saponins used in the monkey studies, acid hydrolyzed in accordance with the present invention, was used to test the effect on intestinal cholesterol absorption in rats. The general procedure is a slight modification of the method as described by D. B. Zilversmit, *Proc. Soc. Exp. Biol. Med.*, 140, 862 (1972), incorporated herein by reference. Twelve male albino Sprague-Dawley rats weighing about 325 g were injected intravenously with 4 $\mu$Ci of [1$\alpha$, 2$\alpha$(in)-$^3$H]-cholesterol (s.a. 60 Ci/mmol, Amersham/Seale, freshly dissolved in 95% ethanol and suspended in 1 ml of saline. Six rats received per gastric tube (a) 0.5 ml of vegetable oil; (b) 2 $\mu$Ci of [4-$^{14}$C]-cholesterol (s.a. 56 mCi/mmol, Amersham/Searle) dissolved with 2 mg of cholesterol in 1.4 ml of 95% ethanol; (c) 20 mg of alfalfa root saponins in 0.7 ml of 95% ethanol; and (d) 1.0 ml of water. The control rats (N=6) received the same without the alfalfa root saponins. Assignment to either treatment was done according to a strictly random order. Blood was obtained from the tail under light ether anesthesia 48 and 72 hr later and the $^{14}$C/$^3$H ratio was determined in the nonsaponifiable extract of plasma.

Feces were collected daily for 3 days following injection, pooled for each rat, and frozen until analyzed. The feces were thawed, mixed with 50% methanol, and homogenized in a blender (Osterizer, Oster Corp., Milwaukee, Wis.); an aliquot by weight (approximately 1 ml) was transferred to a tared 50 ml screw-cap tube. The feces were saponified under reflux with 2 ml of 33% KOH for 1 hr at 100° C.; small condensers were adapted to the screw-cap tubes. The saponified feces were cooled, 2 ml of ethanol were added, and the mixture was extracted into 20 ml of petroleum ether. The solvent was washed with 5 ml of water and an aliquot was dried under $N_2$. The residue was dissolved in chloroform and ozone was dispersed until the color disappeared, thus decreasing quenching considerably. The solvent was dried under $N_2$ and the radioactivity was assayed in 0.5 ml water and 12 ml of 10% Bio-Solv Solubilizer (Beckman Instrument, Fullerton, Calif.). Recovery of added labelled cholesterol to nonradioactive feces was 97.9$\pm$0.4% (mean$\pm$SD, N=4). The amount of $^{14}$C absorbed and then excreted in the nonsaponifiable material was calculated as the product of the nonsaponifiable $^3$H excreted times the average $^{14}$C/$^3$H plasma ratio determined at 48 and 72 hrs, and it was subtracted from the total fecal steroid excretion, thus the calculated fecal sterol excretion corresponds to nonabsorbed cholesterol.

Results

The results obtained in the tests with the monkeys are shown in the FIGURE of the drawing which shows the effect of alfalfa root saponins on plasma cholesterol in *M. fascicularis*. Each point represents the average of 5 animals; bars, S.E.; B-C diet; semi-purified high butter, high cholesterol diet as previously described. During the first dietary intervention without saponins, plasma cholesterol rose from 158$\pm$9 (mean$\pm$S.E.) mg/dl to 213$\pm$8 mg/dl in Group I, and from 146$\pm$6 to 206$\pm$19 mg/dl in Group II. During the second dietary intervention, plasma cholesterol rose from 147$\pm$6 to 203$\pm$10 mg/dl in group I (control) and changed from 154$\pm$10 to 140$\pm$14 mg/dl in Group II (saponin-fed). The difference between the cholesterolemia of the two groups of monkeys was signficant at the end of the experiment (p. "t" test <0.01). Although saponin-fed monkeys showed a tendency to lower body weights than control monkeys, the differences were not significant (Wilcoxon-White rank test).

Results in rats are shown in Table 1. The intestinal absorption of cholesterol in control rats was 70% (average of plasma ratio and fecal sterol excretion methods). Alfalfa root saponins decreased cholesterol absorption to 32%.

TABLE I

| | Effect on alfalfa root saponins on cholesterol absorption in rats (mean $\pm$ S.E.). | | |
|---|---|---|---|
| | Plasma | Fecal $^{14}$C-sterol excretion*** | |
| Group* | $^{14}$C/$^3$H ratio** | (DPM $\times$ 10$^{-3}$ /72 hr/$\mu$Ci) | %O.D.+ |
| a. Controls | 0.68 $\pm$ 0.02++ | 602 $\pm$ 22++ | 27 $\pm$ 1++ |
| b. Saponins | 0.26 $\pm$ 0.02 | 1.359 $\pm$ 36 | 62 $\pm$ 2 |

*Each group consists of 6 animals
**Average of 48 and 72 hrs
***Corrected for intraluminal secretion
+ O.D., oral dose
++ p("t" test) vs experimental group <0.01

The results demonstrate that alfalfa root saponins, prepared in accordance with the present invention, prevent the expected increase in cholesterolemia associated with the injestion of butter and cholesterol in monkeys. The intestinal absorption of cholesterol in the control rats was higher than in previous studies. The disparity may be related to the different diet and pattern of feeding, the intragastric injection of alcohol, the use of smaller amounts of "cold" cholesterol per os, or to other minor methodoligical differences. However, the present results confirm that alfalfa root saponins, prepared in accordance with the present invention, prevent intestinal absorption of cholesterol.

It is thought that the invention and many of its attendant advantages will be understood from the foregoing description, and it will be apparent that various changes may be made in the methods as described herein without departing from the spirit and scope of the invention or sacrificing its material advantages, the forms hereinbefore described being merely preferred embodiments thereof.

The embodiments of the invention in which the exclusive property or privilege is claimed are defined as follows:

1. A method of subjecting saponins to acid hydrolysis under mild conditions to enhance their cholesterol-combining properties comprising:
    (a) dissolving the saponins in an aqueous alcoholic solvent;
    (b) adjusting the acidity of the saponins solution obtained in step (a) to about from 1.2 to 2.0 N;

(c) heating the aqueous alcoholic solution obtained in step (b) until refluxing of the solvent begins and thereafter maintaining the solution at gentle reflux for about from 20 to 60 minutes whereby modified saponins having enhanced cholesterol-combining properties are produced; and (d) recovering the modified saponins obtained in step (c).

2. The method of claim 1, wherein the alcohol is ethanol.

3. The method of claim 1, wherein the aqueous alcoholic solvent consists of a 1:1 mixture of ethanol and water.

4. The method of claim 1, wherein the adjustment of the acidity is carried out by the addition of a mineral acid.

5. The method of claim 4, wherein the mineral acid is a member selected from the group consisting of hydrochloric, nitric, and sulfuric acids.

6. The method of claim 3, wherein the refluxing of the solvent begins at about 90° C.

7. The method of claim 1, wherein the heating at gentle reflux is carried out for about 30 minutes.

8. The method of claim 1, wherein the recovery of the modified saponins in step (d) is carried out by adding an equal volume of water to the solution obtained in step (c) to precipitate the modified saponins, and the precipitate thereafter recovered.

9. The method of claim 8, wherein the precipitate of the modified saponins is recovered by centrifugation.

10. The method of claim 8, wherein the recovered precipitate of the modified saponins is further purified by washing with water to remove any adhering acid, redissolved in hot alcohol, and re-precipitated by addition of water.

11. The method of claim 10, wherein the hot alcohol solution of the re-dissolved precipitate of the modified saponins is decolorized by the addition of a suitable decolorizing agent before re-precipitating the modified saponins.

12. The method of claim 11, wherein the decolorizing agent is charcoal.

13. The method of claim 10, wherein the purified, re-precipitated modified saponins are recovered and dried.

14. The method of claim 1, wherein the saponins dissolved in the aqueous alcoholic solvent comprise saponins from alfalfa roots or tops.

15. The modified saponins produced by the method of claim 1.

* * * * *